(12) United States Patent
Leisinger

(10) Patent No.: US 8,375,555 B2
(45) Date of Patent: Feb. 19, 2013

(54) TORQUE-TURN ORTHOPAEDIC BOLT TIGHTENING METHOD

(75) Inventor: Steven R. Leisinger, Columbia City, IN (US)

(73) Assignee: DePuy Synthes Products, LLC., Warsaw, IN (US)

( * ) Notice: Subject to any disclaimer, the term of this patent is extended or adjusted under 35 U.S.C. 154(b) by 323 days.

(21) Appl. No.: 12/827,389

(22) Filed: Jun. 30, 2010

(65) Prior Publication Data
US 2012/0000063 A1   Jan. 5, 2012

(51) Int. Cl.
*A61B 17/04* (2006.01)
*A61B 17/58* (2006.01)

(52) U.S. Cl. ......... 29/525.11; 606/102; 623/16; 623/18; 623/22; 623/23

(58) Field of Classification Search ................. 29/525.11
See application file for complete search history.

(56) References Cited

U.S. PATENT DOCUMENTS

| | | | |
|---|---|---|---|
| 4,161,221 A | 7/1979 | Carlin et al. | |
| 5,002,578 A * | 3/1991 | Luman | 623/22.42 |
| 5,589,644 A | 12/1996 | Becker et al. | |
| 5,725,533 A | 3/1998 | Carlsson | |
| 6,136,035 A * | 10/2000 | Lob et al. | 623/23.15 |
| 6,319,286 B1 * | 11/2001 | Fernandez et al. | 623/23.18 |
| 6,330,845 B1 | 12/2001 | Meulink | |
| 7,082,866 B2 | 8/2006 | Becker | |
| 7,235,106 B2 | 6/2007 | Daniels et al. | |
| 7,297,166 B2 | 11/2007 | Dwyer et al. | |
| 7,455,695 B2 * | 11/2008 | Khalili et al. | 623/22.42 |
| 7,565,844 B2 | 7/2009 | Crass et al. | |
| 2004/0122440 A1 * | 6/2004 | Daniels et al. | 606/102 |
| 2008/0209707 A1 * | 9/2008 | Cioto et al. | 29/407.02 |
| 2009/0024174 A1 * | 1/2009 | Stark | 606/321 |
| 2009/0139738 A1 | 6/2009 | Lippek | |
| 2010/0106200 A1 * | 4/2010 | Stark | 606/308 |

FOREIGN PATENT DOCUMENTS

| | | |
|---|---|---|
| DE | 202008004730 U1 | 7/2008 |
| EP | 2067576 A2 | 6/2009 |
| FR | 2371679 A1 | 6/1978 |
| GB | 2096361 A | 10/1982 |
| WO | 2009124719 A1 | 10/2009 |

OTHER PUBLICATIONS

Snap-On; Torque Wrench, Electronic, Techangle, Flex Rachet, 12.5 to 250ft. lbs., 1/2" drive; Jun. 3, 2010; 2pgs.

(Continued)

*Primary Examiner* — Livius R Cazan
*Assistant Examiner* — Anthony Green
(74) *Attorney, Agent, or Firm* — Barnes & Thornburg LLP

(57) ABSTRACT

A method of assembling an orthopaedic implant includes positioning a first orthopaedic component in contact with a second orthopaedic component and coupling the first orthopaedic component to the second orthopaedic component with a bolt. The method also includes applying an empirically-determined starting torque to the bolt such that the first orthopaedic component is coupled to the second orthopaedic component with a first predetermined clamp load. The bolt is then rotated by an empirically-determined rotation angle such that the first orthopaedic component is coupled to the second orthopaedic component with a second predetermined clamp load.

10 Claims, 4 Drawing Sheets

OTHER PUBLICATIONS

Boltscience.com; Glossary of Terminology Related to Nuts and Bolts; last visited on Jan. 21, 2010; 2pgs.

Bold Science Limited; Methods of Tightening Threaded Fasteners; last visited on Jan. 12, 2010; 4pgs.

Bold Science Limited; Case Study—Torque Tightening; last visited on Jan. 21, 2010; 2pgs.

Research Council on Structural Connections (RCSC); Specification for Structural Joints Using ASTM A325 or A490 Bolts; Jun. 30, 2004; 94pgs.

European Search Report, European Patent Application No. 11170913.5-2310, Oct. 18, 2011, 6 pages.

* cited by examiner

TORQUE-TURN ORTHOPAEDIC BOLT TIGHTENING METHOD

TECHNICAL FIELD

The present disclosure relates generally to systems and methods for assembling a modular orthopaedic implant.

BACKGROUND

Orthopaedic implants are implanted into patients by orthopaedic surgeons to, for example, correct or otherwise alleviate bone and/or soft tissue loss, trauma damage, and/or deformation of the bone(s) of the patients. Orthopaedic implants may be formed from more than one component, thereby providing the surgeon with a certain degree of flexibility in selecting components that are appropriate to the patient's anatomy.

SUMMARY

According to one aspect of the disclosure, a method of assembling a femoral orthopaedic implant of a hip prosthesis is disclosed. The method includes positioning a femoral neck component in contact with a stem component, passing a bolt through a hollow passageway formed in the femoral neck component, threading the bolt into a threaded bore of the stem component, and tightening the bolt with an empirically-determined starting torque such that a first predetermined clamp load is applied to the femoral neck component and the stem component. The method also includes rotating the bolt by an additional empirically-determined rotation angle such that a second predetermined clamp load is applied to the femoral neck component and the stem component.

In some embodiments, the empirically-determined starting torque may be approximately five Newton-meters. In some embodiments, tightening the bolt with the empirically-determined starting torque may include rotating the bolt approximately forty degrees. Additionally, in some embodiments, the second predetermined clamp load may be within a range of clamp loads having a linear relationship with the rotation angle of the bolt.

According to another aspect, the method of assembling a femoral orthopaedic component of a hip prosthesis includes positioning a femoral neck component in contact with a stem component, joining the femoral neck component to the stem component with a bolt, and threading the bolt into a threaded bore of the stem component. The threaded bore has a longitudinal axis extending therethrough. The method also includes tightening the bolt with an empirically-determined starting torque to place the bolt in a first position about the longitudinal axis, and rotating the bolt by an empirically-determined rotation angle to move the bolt from the first position to a second position about the longitudinal axis.

In some embodiments, tightening the bolt may include creating a first predetermined clamp load. In some embodiments, the first predetermined clamp load may be within a range of 1.5 and 2.0 kilo-Newtons. In some embodiments, rotating the bolt may include creating a second predetermined clamp load. Additionally, in some embodiments, a linear relationship may exist between the rotation angle of the bolt and the clamp load when the bolt is located at the second position about the longitudinal axis.

According to another aspect, a method of assembling an orthopaedic implant is disclosed. The method includes positioning a first orthopaedic component in contact with a second orthopaedic component, and coupling the first orthopaedic component to the second orthopaedic component with a threaded fastener assembly having a threaded shaft. The method also includes applying an empirically-determined starting torque to the threaded fastener assembly such that the first orthopaedic component is coupled to the second orthopaedic component with a first predetermined clamp load. The threaded fastener assembly is rotated by an empirically-determined rotation angle such that the first orthopaedic component is coupled to the second orthopaedic component with a second predetermined clamp load.

In some embodiments, the threaded shaft may extend from the second orthopaedic component, and the threaded fastener assembly may include a nut that receives the threaded shaft. In some embodiments, applying the empirically-determined starting torque may include rotating the nut. In some embodiments, the threaded shaft may be a bolt, and applying the empirically-determined starting torque may include rotating the bolt.

BRIEF DESCRIPTION OF THE DRAWINGS

The detailed description particularly refers to the following figures, in which.

DETAILED DESCRIPTION OF THE DRAWINGS

Figure 1:
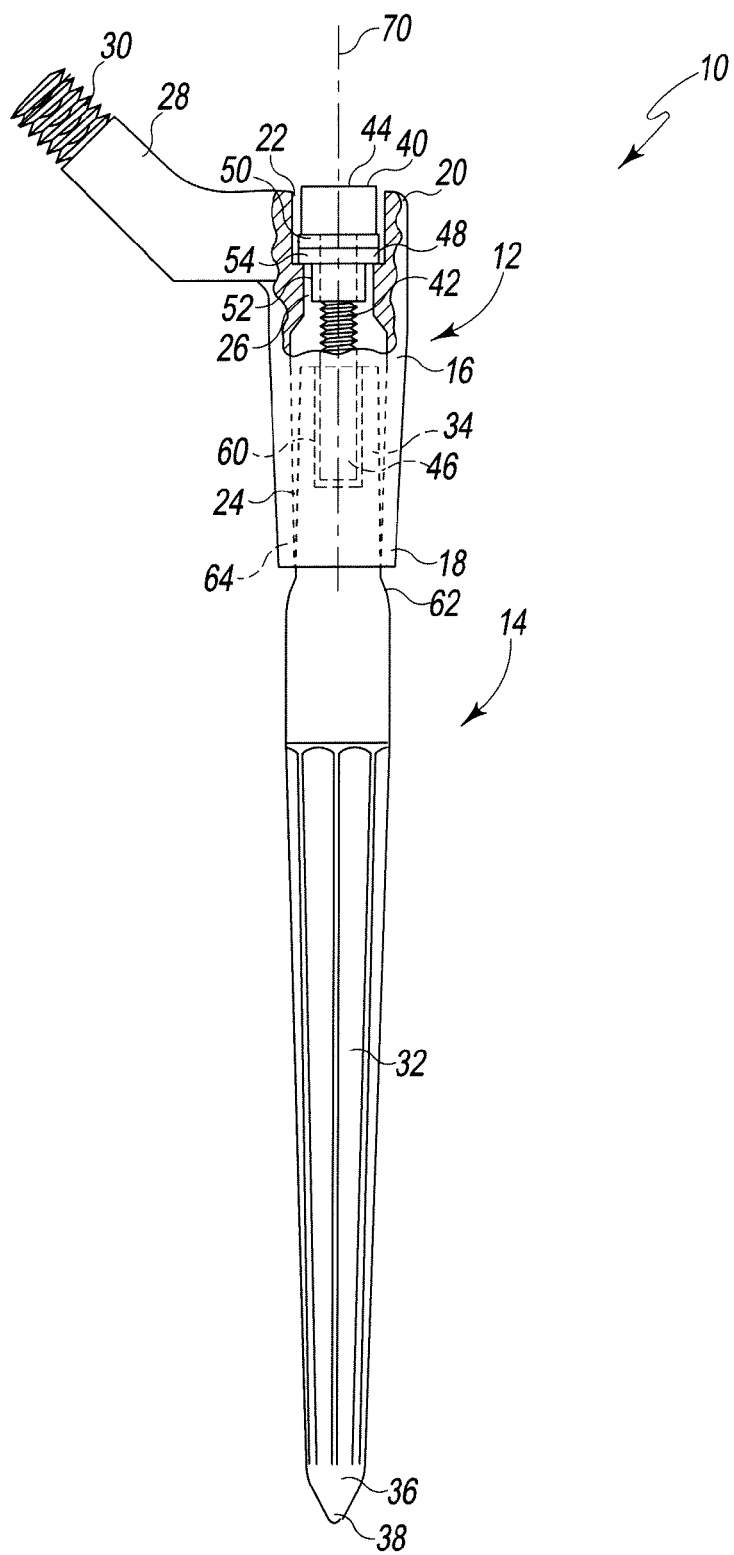
FIG. 1 is a side elevation view of an assembled orthopaedic prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an orthopaedic prosthesis is illustratively embodied as a femoral orthopaedic implant 10 of a hip prosthesis. The femoral orthopaedic implant 10 includes a femoral neck component 12 and a stem component 14 that are configured to be implanted into a patient's femur. The femoral neck component 12 has a body 16 extending from a distal end 18 to a proximal end 20. The body 16 of the femoral neck component 12 includes an aperture 22 formed in the proximal end 20 and an aperture 24 formed in the distal end 18. The apertures 22, 24 are connected via a hollow bore 26 extending therethrough. As shown in FIG. 1, the hollow bore 26 has a smaller diameter than the apertures 22, 24.

A neck 28 extends away from the proximal end 20 of the body 16 to a threaded end 30. The threaded end 30 of the neck 28 receives a ball or head component (not shown) configured to engage with the patient's natural acetabulum or a prosthetic acetabular cup implanted into the patient's pelvic bone. It should be appreciated that in other embodiments the neck 28 may be configured to be press fit, taper fit, or secured by other fastening means to the head component.

The stem component 14 includes a rod 32 extending from a tapered proximal end 34 to a distal end 36. As shown in FIG. 1, the stem component 14 is substantially-straight and has a pointed tip 38 formed at the distal end 36. It will be appreciated that in other embodiments the stem component 14 may have a different configuration to fit the needs of a given patient's anatomy. For example, the stem component 14 may be bowed or have a larger or smaller outer diameter. Similarly, the stem component 14 may be longer or shorter depending on the length of the patient's natural femur.

When assembled as shown in FIG. 1, the proximal end 34 of the stem component 14 is received in the aperture 24 of the neck component 12. The neck component 12 is secured to the stem component 14 via a threaded fastener, which is embodied as a bolt 40. The bolt 40 includes a shaft 42 extending from a bolt head 44 to an externally threaded end 46. As shown in FIG. 1, the shaft 42 extends through a hollow sleeve 48 positioned within the body 16 of the neck component 12 and a lock washer 50 positioned between the sleeve 48 and the bolt head 44. It will be appreciated that in other embodiments the washer 50 may be a flat washer or a Belleville washer. The sleeve 48 includes a cylindrical end 52, which is positioned in the hollow bore 26, and a flange 54, which is placed in contact with the base 56 of the aperture 22.

Figure 3:
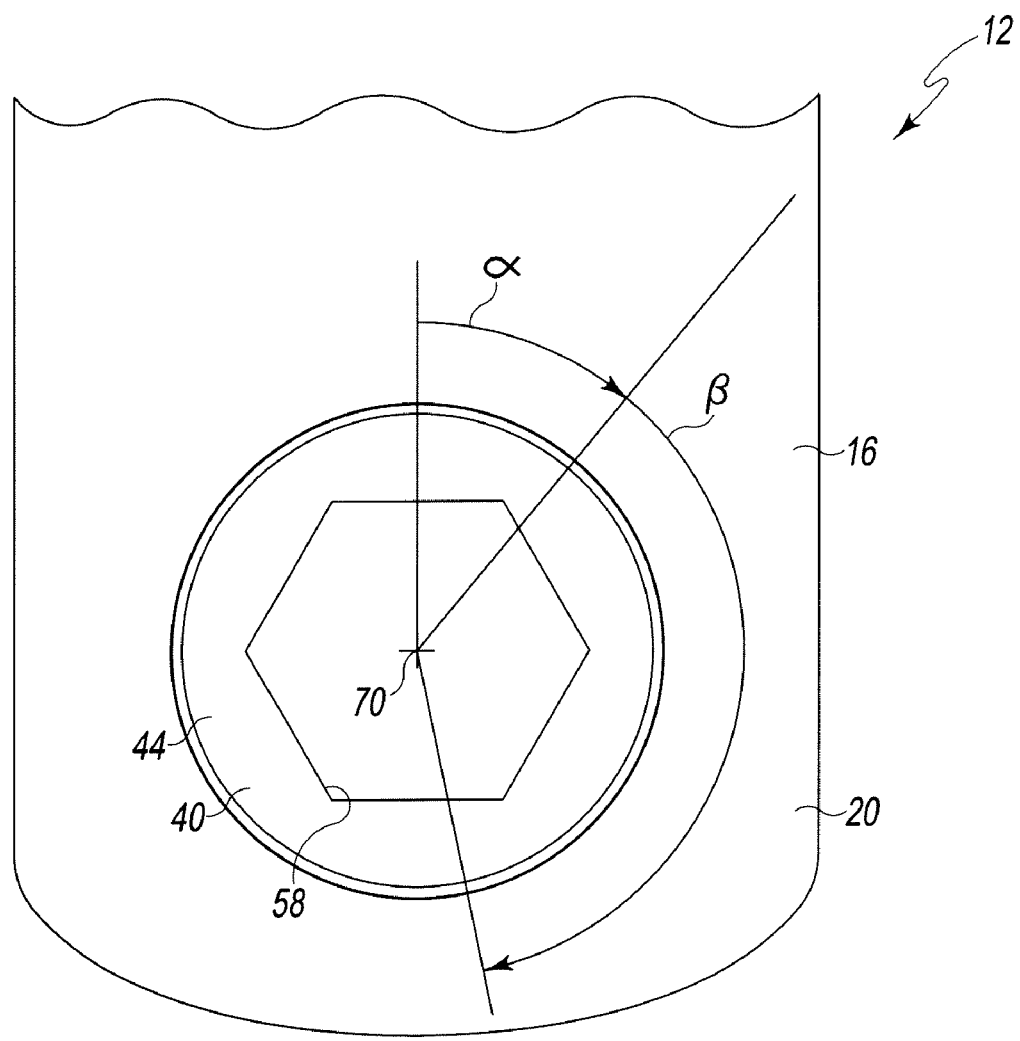
FIG. 3 is a fragmentary top plan view of the orthopaedic prosthesis of FIG. 1 showing the position of the bolt after an empirically-determined starting torque has been applied and the additional rotation of the bolt that is required to achieve a target clamp load.

When fully assembled, the bolt head 44 is positioned in the aperture 22 of the neck component 12. As shown in FIG. 3, the bolt head 44 includes a hex-shaped socket 58 configured to receive a tool having a matching hexagonal cross-section. It will be appreciated that in other embodiments socket 58 may be a double hex-shaped socket, a square-shaped socket, or other suitable socket cross-section. As shown in FIG. 1, the externally threaded end 46 of the bolt 40 is received in an internally threaded aperture 60 formed in the proximal end 34 of the stem component 14.

It will be appreciated that in other embodiments the neck component 12 may be secured to the stem component 14 using other threaded fasteners. For example, the stem component 14 may include an externally-threaded proximal end that extends through the hollow bore 26. In such embodiments, a nut positioned in the aperture 22 would be threaded onto the stem component 14 such that the stem component 14 is secured to the neck component 12.

Figure 2:
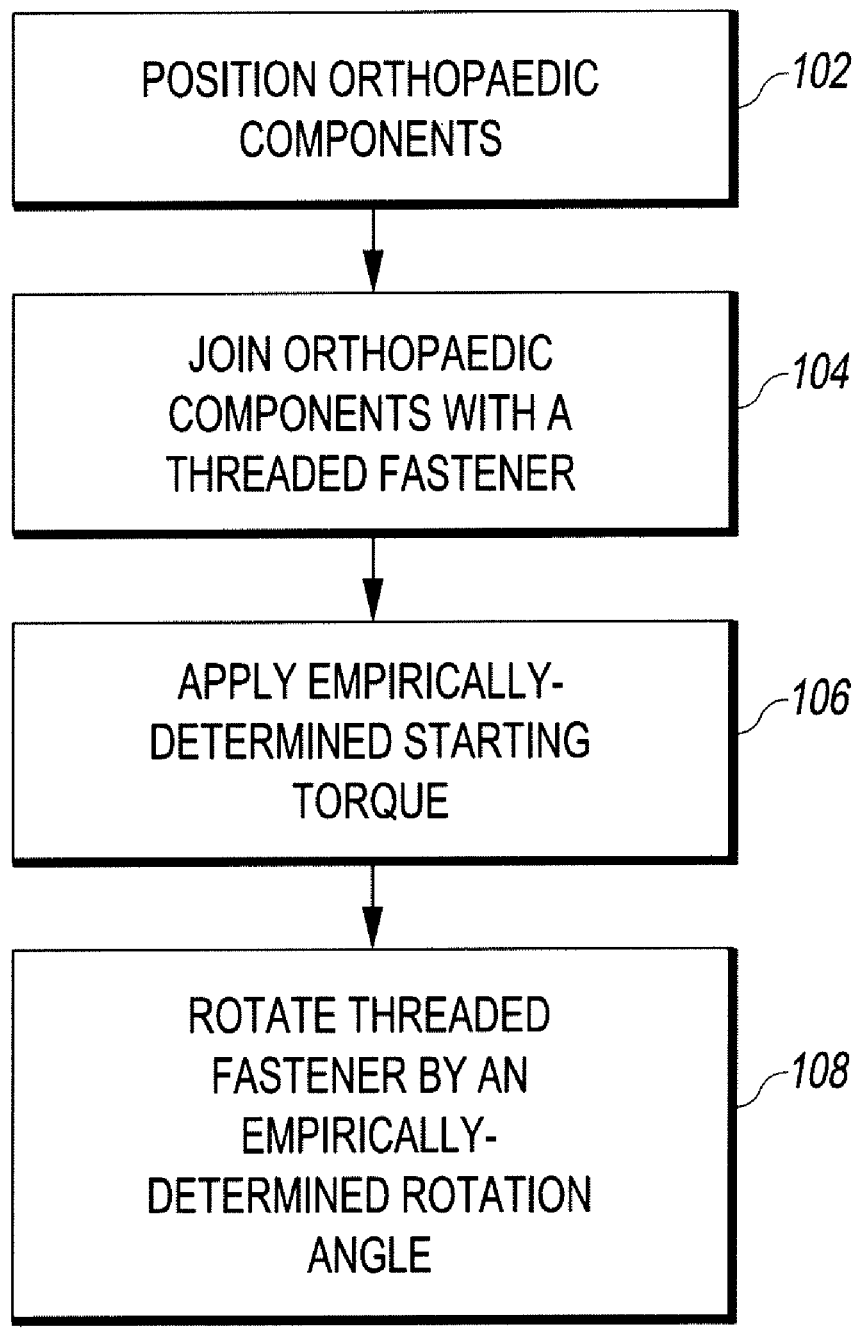
FIG. 2 is one embodiment of a process for assembling the orthopaedic prosthesis of FIG. 1.

Referring now to FIG. 2, a simplified block diagram illustrates a process 100 for assembling the femoral orthopaedic implant 10. In step 102, a surgeon or other medical professional selects the neck component 12 and the stem component 14 appropriate for the patient's anatomy. The surgeon inserts the tapered proximal end 34 of the stem component 14 into the aperture 24 of the neck component 12 until the outer surface 62 of the rod 32 contacts the inner surface 64 of the aperture 24.

In step 104, the sleeve 48 is inserted into the hollow bore 26 of the neck component 12. The lock washer 50 is positioned over the bolt shaft 42 and placed in contact with the bolt head 44. The threaded end 46 of the shaft 42 is then inserted into the aperture 22 and moved through the hollow sleeve 48 into the bore 26. When the threaded end 46 is placed in contact with the threaded aperture 60 of the stem component 14, the surgeon threads the bolt 40 into the stem component 14 by rotating the bolt 40 about the axis 70. The surgeon continues to turn the bolt 40, thereby threading the bolt 40 into the stem component 14 until the bolt head 44 is snug against the base 56 of the aperture 22.

In step 106, the surgeon selects a torque wrench with a hex-head corresponding to the hex socket 58. One example of a torque wrench is the TORQOMETER, U.S./Newton Meter Basic 8.4 Newton-meter (75 inch-pound) torque wrench, Stock No. TER6A, which is commercially available from Snap-on Incorporated of Kenosha, Wis., U.S.A. After engaging the hex-head of the torque wrench with the socket 58, the surgeon uses the torque wrench to rotate the bolt 40, thereby tightening the bolt 40 and applying a clamp load to the neck component 12 and the stem component 14. Using the dial indicator of the torque wrench to determine the amount of torque applied, the surgeon rotates the bolt 40 until an empirically-determined starting torque is applied. The term "empirically-determined starting torque" is defined as the minimum amount of torque required to create a clamp load within a range of clamp loads having a linear relationship with the bolt head rotation angle. As will be described in greater detail below, the empirically-determined starting torque is approximately five Newton-meters in the illustrative embodiment. When the empirically-determined starting torque is applied, the bolt 40 is rotated about the axis 70 by an angle $\alpha$, as shown in FIG. 3. In the illustrative embodiment, the angle $\alpha$ is approximately forty degrees.

In step 108, the surgeon selects a torque angle gauge with a hex-head corresponding to the hex socket 58. One example of a torque angle gauge is the Torque Angle Gauge, Stock No. TA360, which is commercially available from Snap-on Incorporated of Kenosha, Wis., U.S.A. After engaging the hex-head of the torque angle gauge with the socket 58, the surgeon uses the torque angle gauge to rotate the bolt 40 by an empirically-determined rotation angle, which is illustrated in FIG. 3 as an angle $\beta$. The "empirically-determined rotation angle" is defined as the rotation angle of the threaded fastener required to increase the applied clamp load to a target predetermined clamp load. The target predetermined clamp load is set by the orthopaedic prosthesis manufacturer and is based on the operational requirements of the orthopaedic prosthesis. In the illustrative embodiment, the target predetermined clamp load is within the range of clamp loads having a linear relationship with the rotation angle of the bolt.

Figure 4:
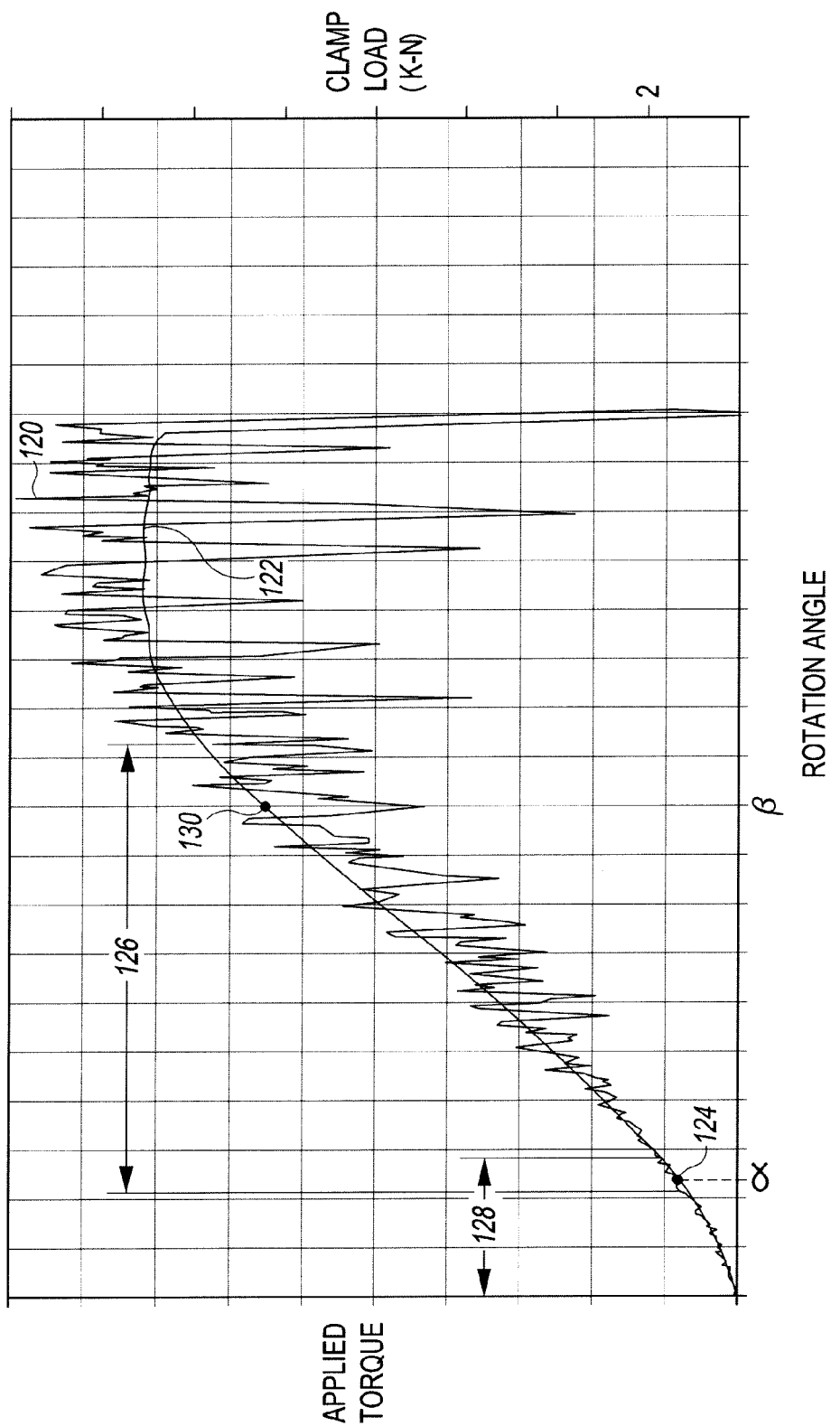
FIG. 4 is a graph showing relationship between clamp load, input torque, and fastener rotation angle.

Referring now to FIG. 4, a graph is illustrated showing the relationship between the clamp load, the applied torque, and the fastener rotation angle. A line 120 illustrates the relationship between the torque applied to the bolt 40 and the rotation angle. A line 122 illustrates the relationship between the clamp load and the rotation angle of the bolt 40. As discussed above, applying the empirically-determined starting torque in step 104 creates an initial predetermined clamp load 124. The initial predetermined clamp load 124 is within a range of clamp loads 126 having a linear relationship between clamp load and rotation angle of the bolt. In that way, when the bolt is further rotated about the axis 70, the clamp load increases linearly as the bolt is rotated. The initial predetermined clamp load 124 is also within a range of clamp loads 128 where the amount of torque applied to the bolt is proportional to the clamp load. As shown in FIG. 4, the torque applied becomes more volatile beyond the range of clamp loads 128.

In the illustrative embodiment, the initial predetermined clamp load 124 is between 1.5 and 2.0 kilo-Newtons. When the surgeon rotates the bolt 40 by the empirically-determined rotation angle $\beta$ in step 108, the target predetermined clamp load 130 is created between the neck component 12 and the stem component 14.

The assembly method set forth above employs a torque wrench and an angle gauge. It will be appreciate that in other embodiments a single wrench may be used to carry out both steps. One example of such a wrench is the TECHANGLE Torque Wrench, Stock No. ATECH3FR250, which is commercially available from Snap-on Incorporated of Kenosha, Wis., U.S.A.

While the assembly method set forth above has been described in relation to a femoral neck implant, it will be appreciated that the assembly method may be used with other orthopaedic prostheses. For example, a surgeon may use a similar assembly method to assemble the components of a tibial orthopaedic implant, a shoulder orthopaedic implant, or any other implant utilized in replacement procedures at other joint locations throughout the body.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A method of assembling a femoral orthopaedic implant of a hip prosthesis, comprising:
    positioning a femoral neck component in contact with a stem component,
    passing a bolt through a hollow passageway formed in the femoral neck component,
    threading the bolt into a threaded bore of the stem component,
    tightening the bolt with an empirically-determined starting torque such that a first predetermined clamp load is applied to the femoral neck component and the stem component, and
    rotating the bolt by an additional empirically-determined rotation angle such that a second predetermined clamp load is applied to the femoral neck component and the stem component,
    wherein tightening the bolt with the empirically-determined starting torque includes rotating the bolt approximately 40 degrees.

2. The method of claim 1, wherein the empirically-determined starting torque is approximately 5 Newton-meters.

3. The method of claim 1, wherein the second predetermined clamp load is within a range of clamp loads having a linear relationship with the rotation angle of the bolt.

4. A method of assembling a femoral orthopaedic component of a hip prosthesis, comprising:
    positioning a femoral neck component in contact with a stem component,
    joining the femoral neck component to the stem component with a bolt,
    threading the bolt into a threaded bore of the stem component, the threaded bore having a longitudinal axis extending therethrough,
    tightening the bolt with an empirically-determined starting torque to place the bolt in a first position about the longitudinal axis, and
    rotating the bolt by an empirically-determined rotation angle to move the bolt from the first position to a second position about the longitudinal axis,
    wherein tightening the bolt includes creating a first predetermined clamp load, the first predetermined clamp load being within the range of 1.5 and 2.0 kilo-Newtons.

5. The method of claim 4, wherein rotating the bolt includes creating a second predetermined clamp load.

6. The method of claim 4, wherein a linear relationship exists between the rotation angle of the bolt and the clamp load when the bolt is located at the second position about the longitudinal axis.

7. A method of assembling an orthopaedic implant, comprising:
    positioning a first orthopaedic component in contact with a second orthopaedic component,
    coupling the first orthopaedic component to the second orthopaedic component with a threaded fastener assembly, the threaded fastener assembly including a threaded shaft,
    applying an empirically-determined starting torque to the threaded fastener assembly such that the first orthopaedic component is coupled to the second orthopaedic component with a first predetermined clamp load, and
    rotating the threaded fastener assembly by an empirically-determined rotation angle such that the first orthopaedic component is coupled to the second orthopaedic component with a second predetermined clamp load
    wherein the first predetermined clamp load is within the range of 1.5 and 2.0 kilo-Newtons.

8. The method of claim 7, wherein the threaded shaft extends from the second orthopaedic component, and the threaded fastener assembly includes a nut that receives the threaded shaft.

9. The method of claim 8, wherein applying the empirically-determined starting torque includes rotating the nut.

10. The method of claim 7, wherein the threaded shaft is a bolt, and applying the empirically-determined starting torque includes rotating the bolt.

* * * * *